United States Patent [19]

Chanoch

[11] Patent Number: 5,569,214
[45] Date of Patent: Oct. 29, 1996

[54] DOSE SETTING KNOB ADAPTER FOR MEDICATION DELIVERY PEN

[75] Inventor: Lawrence H. Chanoch, Mahwah, N.J.

[73] Assignee: Becton Dickinson and Company, Franklin Lakes, N.J.

[21] Appl. No.: 309,378

[22] Filed: Sep. 20, 1994

[51] Int. Cl.$^6$ .................................................. A61M 5/00
[52] U.S. Cl. .......................... 604/246; 604/207; 604/211
[58] Field of Search .................................. 604/246, 232, 604/243, 189, 208–211, 187, 192, 197, 198, 200, 201, 71, 72, 207

[56] References Cited

U.S. PATENT DOCUMENTS

| | | | |
|---|---|---|---|
| 4,563,178 | 1/1986 | Santeramo | 604/208 |
| 5,279,585 | 1/1994 | Balkwill | 604/207 |

*Primary Examiner*—Randall L. Green
*Assistant Examiner*—V. Alexander
*Attorney, Agent, or Firm*—Alan W. Fiedler

[57] ABSTRACT

A dose setting knob adapter for use on a medication delivery pen to convert the small, discrete dose setting control knob into an enlarged T-shaped handle that is easily rotated during dosage setting by a patient with reduced physical skills. The dose setting knob adapter attaches to the clip of the medication delivery pen for storage and mounts with the cap onto the dose setting knob over the proximal end of the medication delivery pen to permit a user to easily manipulate the dose setting knob during dosage setting. The enlarged handle is useful during drug injection since it provides a larger surface for the user to hold during injection. In addition, since the adapter mounts on the clip of the pen's cap during storage, the portable and discrete usage design approach is not compromised.

7 Claims, 5 Drawing Sheets

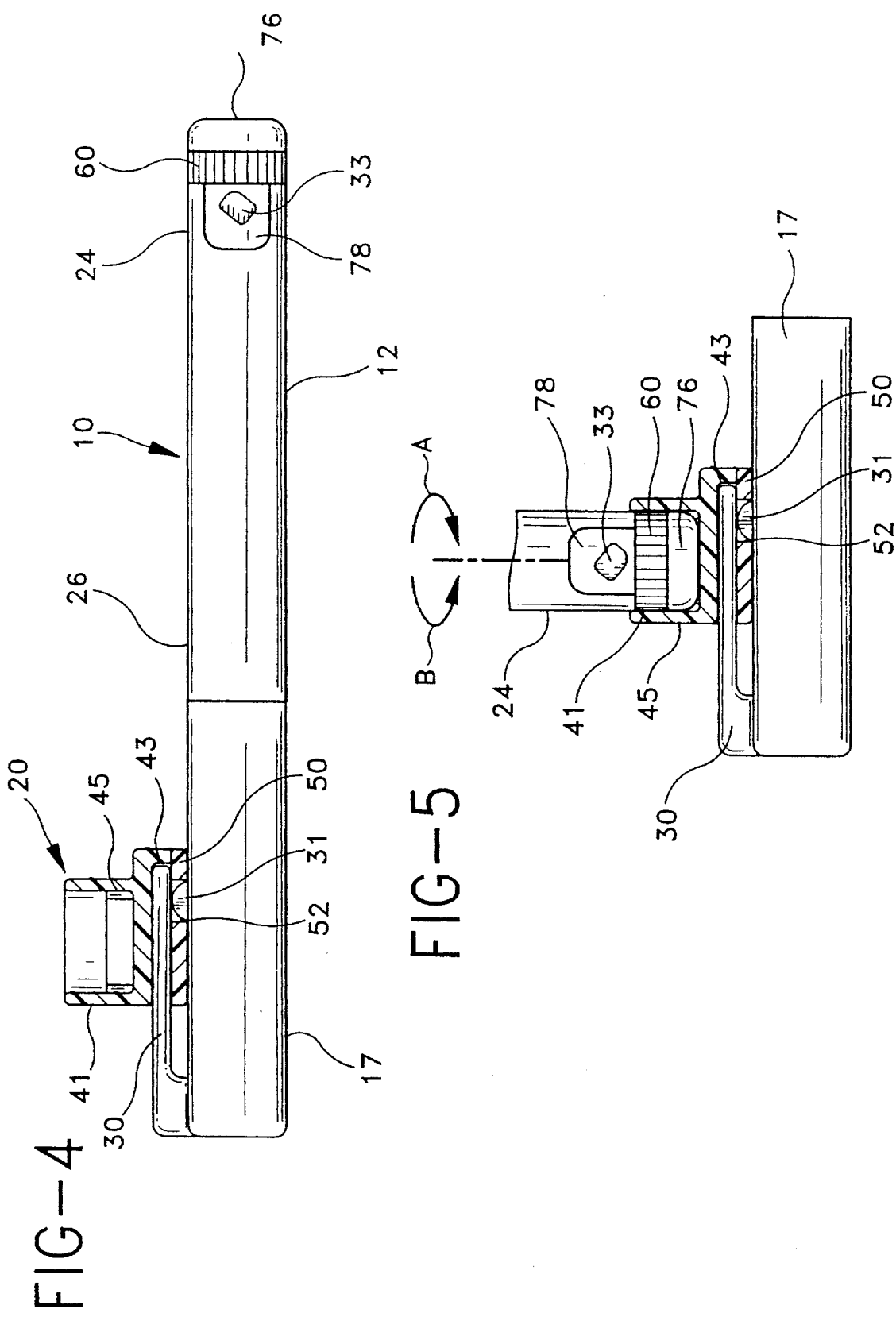

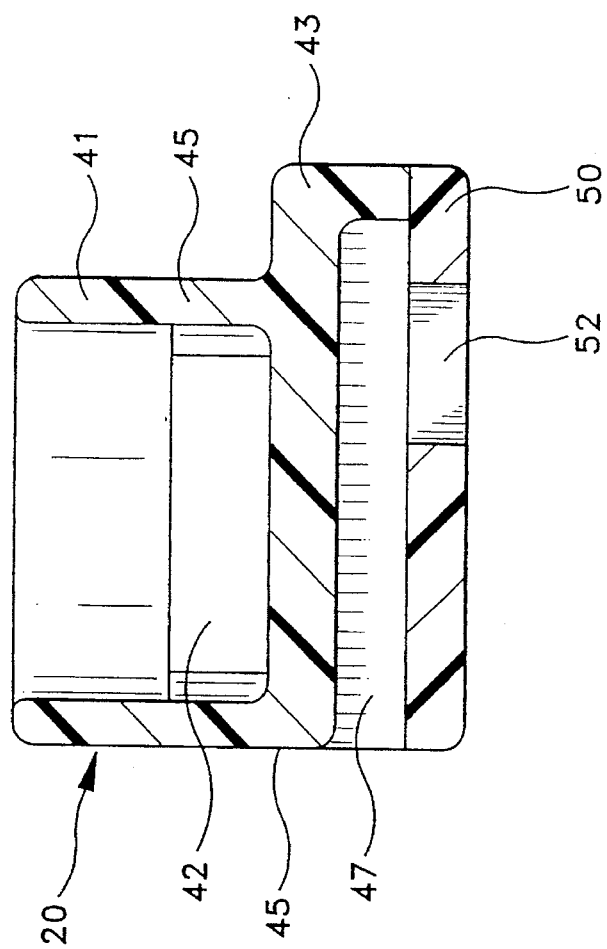
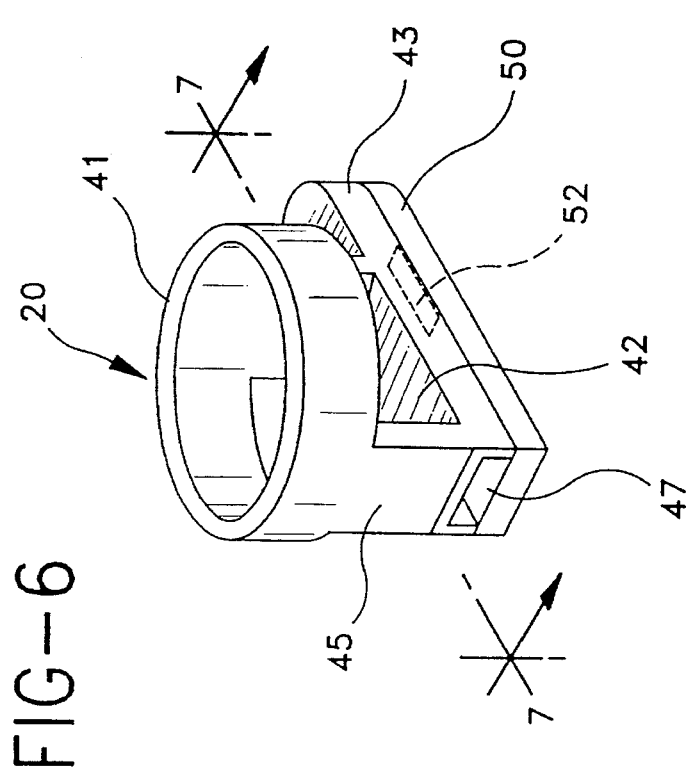

5,569,214

DOSE SETTING KNOB ADAPTER FOR MEDICATION DELIVERY PEN

BACKGROUND OF THE INVENTION

1. Field of the Invention

The subject invention relates to an adapter for use on the dose setting knob of medication delivery pens to provide improved control when setting a selected dose of medication.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula may be mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication may be drawn into the chamber of the syringe barrel by moving the plunger a selected distance in a proximal direction. The needle cannula may be withdrawn from the vial, and the medication may be injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a driver and dose setting apparatus as explained further below. A disposable vial for use with the prior art vial holder includes a distal end having a pierceable elastomeric seal that can be pierced by one end of a double-ended needle cannula. The proximal end of this prior art vial includes a plunger slidably disposed in fluid tight engagement with the cylindrical wall of the vial. This prior art medication delivery pen is used by inserting the vial of medication into the vial holder. A prior art pen body then is connected to the proximal end of the vial holder. The pen body includes a dose setting apparatus for designating a dose of medication to be delivered by the pen and a driving apparatus for urging the plunger of the vial distally for a distance corresponding to the selected dose.

The user of the pen mounts a prior art double-ended needle cannula to the distal end of the vial holder such that the proximal point of the needle cannula pierces the elastomeric seal on the vial. The patient then selects a dose and operates the pen to urge the plunger distally to deliver the selected dose. The dose selecting apparatus returns to zero upon injection of the selected dose with this prior art medication delivery pen. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above.

The above described reusable medication delivery pen is effective and much more convenient for self-administration of medication than the typical hypodermic syringe and separate medication vial. However, the disassembly of the pen to remove empty medication vials and to insert new ones is an inconvenience. As a result, disposable pens have been developed. The prior art disposable medication delivery pen includes a vial of insulin or other such medication permanently encapsulated therein. The patient need merely connect a double-ended needle cannula to the disposable pen for each administration of medication. The prior art disposable pen can be discarded when the supply of medication permanently encapsulated therein has been exhausted.

Disposable medication delivery pens offer certain conveniences to the patient who is required to self-administer medication. However, many pen injectors are designed to be as small as possible to satisfy patients with a need for portability and discrete use. Since it is particularly common among patients with diabetes to have complications of the disease that may have created reduced manual and/or physical skills, many are unable to manipulate the above prior art devices. Hence, it is necessary to provide a medication delivery pen having features that make it easier for a user to manipulate when setting a desired dose for injection.

SUMMARY OF THE INVENTION

The subject invention relates to a dose setting knob adapter for use on a medication delivery pen to convert the small, discrete dose setting control knob into an enlarged T-shaped handle that is easily rotated during dosage setting by a patient with reduced physical skills. The dose setting knob adapter attaches to the clip of the delivery pen for storage and mounts on the dose setting knob at the proximal end of the delivery pen to permit a user to easily manipulate the dose setting knob during dosage setting. It improves user manipulation by enlarging the dose setting control surface from a small knob that is difficult to manipulate into a large T-shaped handle that requires almost no manually dexterity to successfully rotate during the dosage setting operation. The enlarged handle is also useful during the drug injection procedure, since it provides a larger surface for the user to hold onto during injection. In addition, since the adapter mounts on the clip of the pen's cap during storage, the portable and discrete usage design approach is not compromised. The cap could also be attached to the dose setting knob using other means such as by a tab, socket, or gripper ring.

The present invention also provides means for establishing and precisely controlling the amount of medication to be delivered in response to each actuation of an actuator button on the delivery pen, since the adapter on the cap enlarges the dose setting knob into a T-shaped handle that provides a larger surface for the user to hold during injection. In addition, since the adapter mounts on the clip of the pen cap during storage, the portable and discrete usage design approach for such medication delivery pens is not compromised.

DESCRIPTION OF THE DRAWINGS

FIG. 4 is an elevational and partial cross-sectional view of the medication delivery pen and adapter shown in FIG. 2.

FIG. 5 is an enlarged elevational and partial cross-sectional view of the adapter mounted on the dose setting knob of the medication delivery pen shown in FIG. 4.

FIG. 6 is an enlarged perspective view of the adapter.

FIG. 7 is a cross-sectional view of the adapter taken along line 7—7 in FIG. 6.

DETAILED DESCRIPTION

Figure 1:
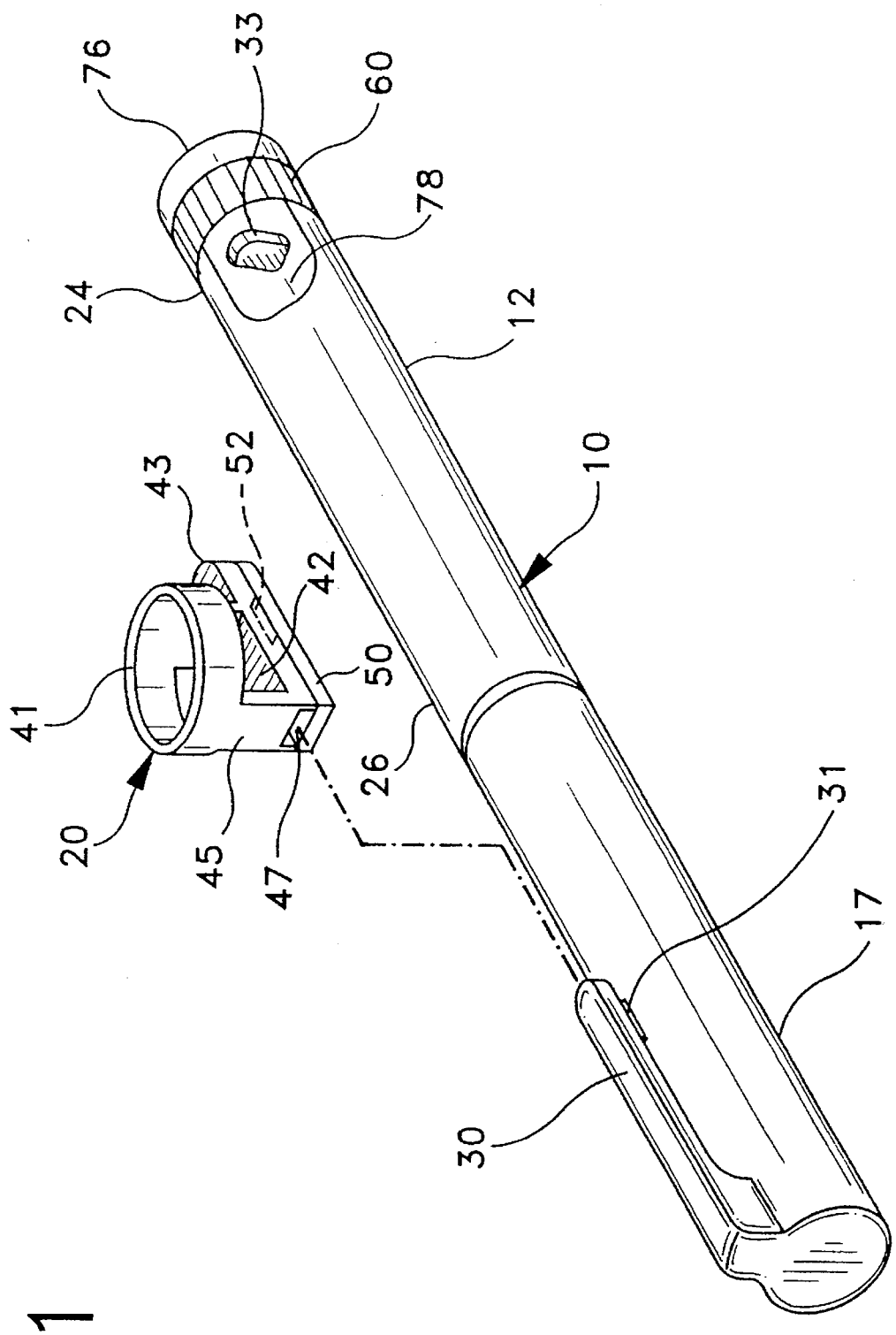
FIG. 1 is an exploded view of a medication delivery pen and an adapter of the subject invention, with the adapter removed.

An adapter 20 and medication delivery pen 10 in accordance with the subject invention are shown in the exploded view in FIG. 1 with adapter 20 removed. Medication delivery pen 10 includes a pen body assembly 12, having opposed proximal and distal ends 24 and 26, respectively, with a shielding cap 17 attached to distal end 26. Shielding cap 17 includes a clip 30 with a locking protrusion 31 located underneath clip 30 that is used to attach a capped medication delivery pen 10 to a flat surface during storage or transportation.

A window insert 78 is mounted in the side of pen body assembly 12 at proximal end 24 and includes a cut-out or window 33 through which a user may view dosage indicia (not shown) therein. The dosage indicia is used by the user to set the dosage desired for the next injection. A rotatable dose setting knob 60 is inserted through proximal end 24 of pen body assembly 12, with the proximal end of dose setting knob 60 being characterized by a gnarled exterior surface to facilitate manipulation for setting a selected dose. As mentioned above, window 33 is disposed in insert 78 on the side of pen body assembly 12 to enable dosage indicia on dose setting knob 60 to be visible by the user through window 33, when the user is setting a desired dose. The desired dose of medication is set by the user rotating dose setting knob 60 until the desired dosage indicia corresponding to the desired dose appears in window 33 of insert 78.

An actuator button 76 is rotatably attached to the proximal end of dose setting knob 60 for use by the user when performing an injection after a desired dose has been set. During injection the user inserts a distal point 124 of a needle cannula 126, shown in FIG. 3, into their body and injects the dosage indicated by the indicia showing through window 33 by merely pushing actuator button 76 into proximal end 24 of pen body assembly 12.

Adapter 20, as shown in FIG. 1, includes a receiving ring 41 for receiving the proximal end of dose setting knob 60 such that when adapter 20 is rotated dose setting knob 60 is directly driven and rotated in the same direction. Receiving ring 41 is attached to a base portion 43 by a pair of posts 45 with a space 42 therebetween for receiving actuator button 76 so that receiving ring 41 does not contact actuator button and only rotates dose setting knob 60. Base portion 43 includes a substantially hollow bore 47 closed by a lower surface 50 along its bottom. Lower surface 50 includes a locking hole 52 therethrough for receiving a locking protrusion 31 on cap 17, discussed below.

Figure 2:
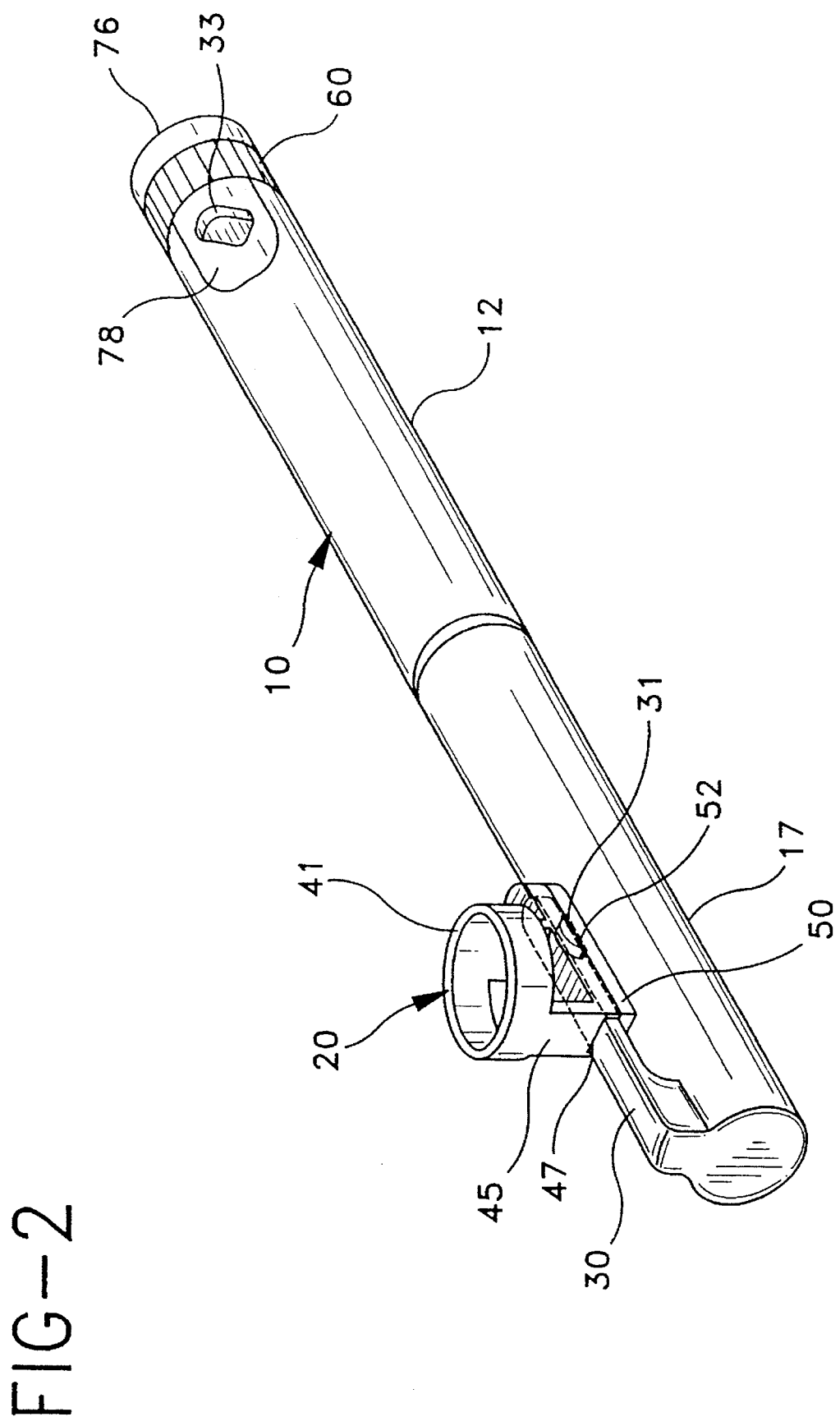
FIG. 2 is a perspective view of the medication delivery pen and adapter shown in FIG. 1, with the adapter attached.

FIG. 2 is a perspective view of medication delivery pen 10 and adapter 20 shown in FIG. 1, and shows adapter 20 attached to clip 30. FIG. 2 more clearly shows the interaction between adapter 20 and clip 30, with clip 30 contained within bore 47 in base portion 43 and locking protrusion 31 of cap 17 received in locking hole 52 in lower portion 50. When locking protrusion 31 is contained in locking hole 52, adapter 20 is retained on clip 30 and can not be removed without considerable force being applied to cap 17 and adapter 20 in opposite directions.

Figure 3:
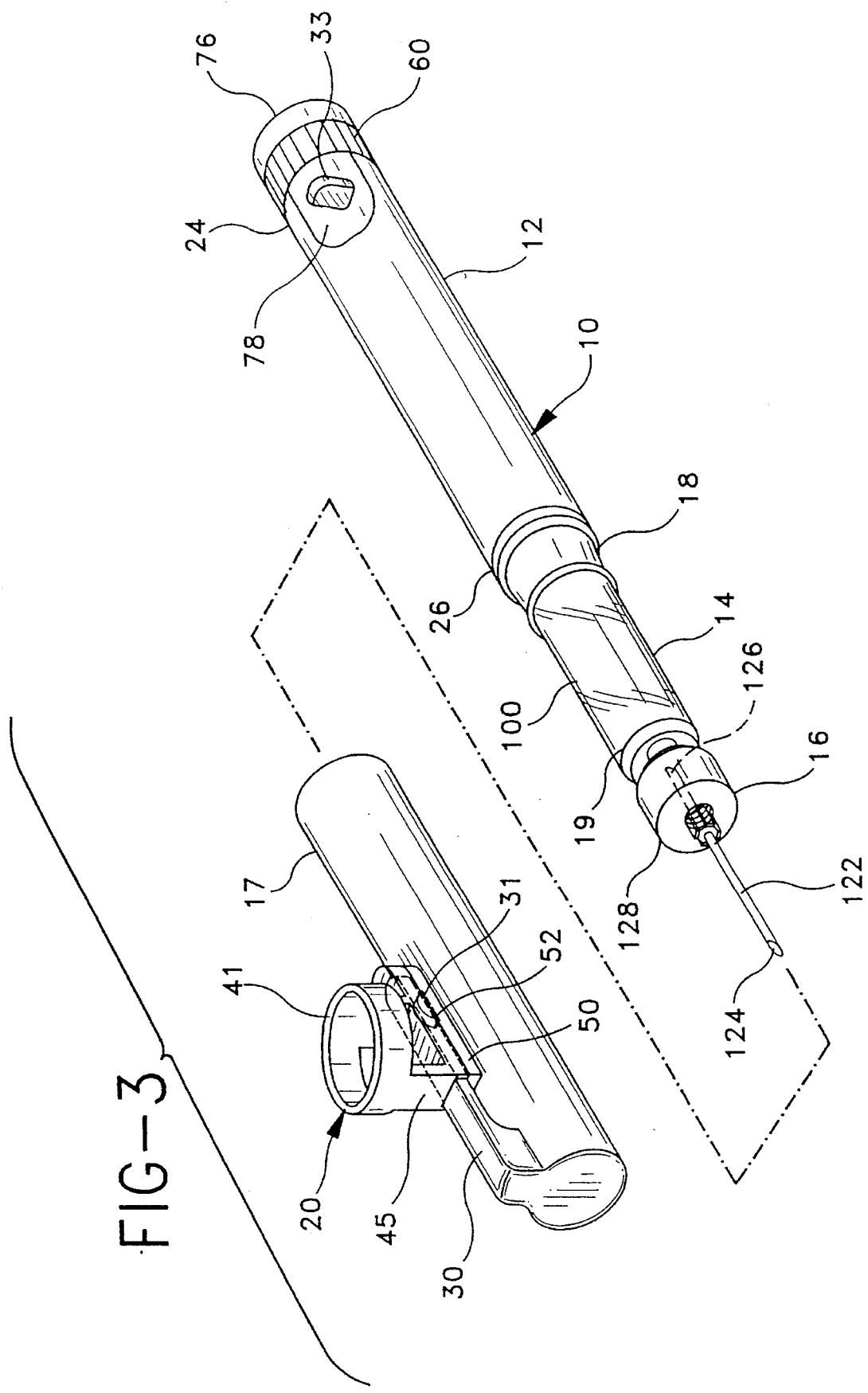
FIG. 3 is a perspective view of the medication delivery pen and adapter shown in FIGS. 1 and 2, with the cap removed.

FIG. 3 is a perspective view of medication delivery pen 10 and adapter 20 shown in FIGS. 1 and 2, with cap 17 removed. FIG. 3 shows the additional portions of medication delivery pen 10 located at its distal end that are covered by cap 17, when it is attached to distal end 26 of pen body assembly 12. As shown in FIG. 3, medication delivery pen 10 also includes a disposable cartridge holder assembly 14 dimensioned and configured to threadedly engage pen body assembly 12 at proximal end 18. Cartridge holder assembly 14 including a medication cartridge (not shown) securely retained in a housing 100 that contains a volume of medication to be injected by the user.

Medication delivery pen 10 also includes a needle cannula assembly 16 that is releasable engaged to a distal end 19 of cartridge holder assembly 14. Needle cannula assembly 16 has a double ended needle cannula 122 having a distal point 124 and a proximal point 126 extending into cartridge holder assembly 14. Proximal point 126 piercing a seal on the mediation cartridge within cartridge holder assembly 14. A lumen extends between proximal point 26 and distal point 24 of needle cannula assembly 16 through a mounting hub 128. Needle cannula assembly 16 being mounted on distal end 19 of cartridge holder assembly 14 by mounting hub 128. When cap 17 is attached to distal end 26 of pen body assembly 12, needle cannula assembly 16 and cartridge holder assembly 14 are both enclosed within cap 17 during storage and transportation.

In a preferred embodiment, pen body assembly 12 is reusable, and cartridge holder assembly 14 is disposable, however, other arrangements could also be used in accordance with the present invention. As noted above, cartridge holder assembly 14 contains the medication cartridge with a volume of medication sufficient for administration of several doses. Therefore, after exhaustion of the medication, cartridge holder assembly 14 can be threadedly disengaged from pen body assembly 12 and discarded, with a new cartridge holder assembly 14 being mounted to the pen body assembly 12 for future injections. The assembled pen body assembly 12, cartridge holder assembly 14 and cap 17 may then be stored and/or carried until another selected dose of medication is required.

FIG. 4 is an elevational and partial cross-sectional view of medication delivery pen 10 and adapter 20 that more clearly shows the interaction between locking hole 52 in lower portion 50 of base portion 43 and locking protrusion 31 extending from cap 17 underneath clip 30. Just prior to use, cap 17 is removed from pen body assembly 12 and a needle cannula assembly 16 is threadedly engaged to distal end 19 of cartridge holder assembly 14. As needle cannula assembly 16 is threadedly engaged to distal end 19, proximal point 126 of double ended needle cannula 122 pierces the seal on the medication cartridge within cartridge holder assembly 14, and provides a communication path for the medication within the medication cartridge.

The user then sets a desired dose of medication by rotating dose setting knob 60 until indicia corresponding to the desired dose appears in window 33 of insert 78. As dose setting knob 60 is rotated it extends out of or from proximal end 24 of pen body assembly 12 a distance corresponding to the dosage being set. When the desired dose is set, injection is achieved by merely pushing on actuator button 76. This causes dose setting knob 60 to turn relative to pen body housing 12 in a direction that is opposite to the direction of rotation generated by the dose setting procedure. As dose setting knob 60 enters proximal end 24 of pen body assembly 12, a plunger (not shown) is urged distally into the medication cartridge and causes medication in the cartridge to be injected through needle cannula 122 into the user. Injection is terminated when dose setting knob 60 engages proximal end 24 of pen body housing 12, the position shown in FIG. 3.

After injection is complete, needle cannula assembly 16 may be disengaged from cartridge holder assembly 14 and safely discarded. Cap 17 may be mounted over cartridge holder assembly 14, and capped medication delivery pen 10 may be stored or carried in a convenient location until the next dose of medication is required. A subsequent dose of medication will be set in exactly the manner as described above, and dose setting and injections can be carried out until all medication has been used. Cartridge holder assembly 14 may then be threadedly disengaged from pen body assembly 12, and discarded and replaced as described above.

FIG. 5 is an enlarged elevational view of proximal end 24 of medication delivery pen 10 in a use position with a cross-sectional view of adapter 20 attached thereto. During use, adapter 20 is attached to clip 30 on cap 17 and then attached to proximal end 24 of pen body assembly 12. When adapter 20 is attached, as shown in FIG. 5, it provides the user with a very functional T-shaped handle that provides efficient means for a user to rotate dose setting knob 60 and easily set a desired dosage of medication for injection. FIG. 5 also more clearly shows the relationship between locking hole 52 and locking protrusion 31, and that receiving ring 41 is sufficiently spaced above base portion 43 by posts 45 so that attachment ring 41 mounts onto dose setting knob 60 and space 42 of adapter 20 receives actuator button 76. This arrangement provides for the rotation of cap 17 to cause dose setting knob 60 to rotate with adapter 20. As shown, rotation of cap 17 and adapter 20 can be in the direction of arrow A or the direction of arrow B, depending on whether the dosage amount is being increased or decreased.

FIG. 6 is an enlarged perspective view of only adapter 20 and FIG. 7 is a cross-section view of adapter 20 taken along lines 7—7 in FIG. 6, with both FIGS. 6 and 7 more clearly showing the above-mentioned features of adapter 20. For example, bore 47 is shown extending into base portion 43 with its lower surface 50 including locking hole 52 for receiving protrusion 31 on cap 17. FIGS. 5 and 6 also show the pair of posts 45 connecting receiving ring 41 to base portion 43 with space 42 located therebetween.

While the present invention has been described with respect to a preferred embodiment, it is apparent that various changes can be made without departing from the scope of the invention as defined by the appended claims. For example, the adapter and cap can plug into the dose setting knob in a variety of ways such as by a tab, socket, or gripper ring. Other various optional constructions will be apparent to those skilled in the art after having read the subject disclosure.

What is claimed is:

1. An adapter for use on a medication delivery pen to provide improved control when setting a selected dosage of a medication to be delivered by the medication delivery pen, said adapter comprising:

means for attaching said adapter to a cap on a medication delivery pen; and means for receiving a dose setting knob on the medication delivery pen, said receiving means comprising a receiving ring extending from said attaching means, said receiving ring being capable of receiving the dose setting knob so that when the cap attached to said adapter is rotated the dose setting knob is rotated and a desired dosage of medication to be delivered by the medication delivery pen can be set.

2. An adapter according to claim 1, wherein said means for attaching said adapter to the cap of the medication delivery pen attaches to a clip on the cap.

3. An adapter according to claim 1, wherein said means for attaching said adapter to the cap of the medication delivery pen comprises a base portion having a bore for receiving a clip on the cap.

4. An adapter according to claim 3, wherein said means for attaching said adapter to the cap of the medication delivery pen further comprises a locking hole in a lower surface of the base portion for receiving a locking protrusion extending from the cap underneath the clip.

5. An adapter according to claim 3, further comprising a post connecting said receiving ring to said base portion so that said receiving ring receives the dose setting knob.

6. A combination of a medication delivery pen and an adapter comprising:

a pen body assembly having a distal end and a proximal end;

a needle assembly attached to the distal end of said pen body assembly;

a dose setting knob rotatably attached to the proximal end of said pen body assembly for setting a dosage of medication to be delivered from said pen body assembly;

a cap releasably attached to and covering the distal end of said pen body assembly to cover said needle assembly when not in use; and an adapter comprising:
      means for attaching said adapter to said cap; and
      means for receiving said dose setting knob, said receiving means comprising a receiving ring extending from said attaching means, said receiving ring being capable of receiving the dose setting knob so that when said cap attached to said adapter is rotated the dose setting knob is rotated and a desired dosage of medication to be delivered by the medication delivery pen can be set.

7. An adapter according to claim 6, wherein said cap includes a clip and said means for attaching said adapter to said cap of said pen body assembly comprises a base portion having a bore for receiving said clip on said cap.

* * * * *